United States Patent
Wang et al.

(10) Patent No.: US 11,766,325 B2
(45) Date of Patent: Sep. 26, 2023

(54) PROSTHETIC HEART VALVE COOLING

(71) Applicant: Medtronic Vascular, Inc., Santa Rosa, CA (US)

(72) Inventors: Wei Wang, Santa Rosa, CA (US);
Benjamin Wong, Santa Rosa, CA (US);
Laura McKinley, Santa Rosa, CA (US);
Joshua Dudney, Santa Rosa, CA (US);
Tracey Tien, Santa Rosa, CA (US);
Karl Olney, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 17/747,292

(22) Filed: May 18, 2022

(65) Prior Publication Data
US 2022/0273425 A1 Sep. 1, 2022

Related U.S. Application Data

(63) Continuation of application No. 16/854,095, filed on Apr. 21, 2020, now Pat. No. 11,364,115, which is a continuation of application No. 16/123,047, filed on Sep. 6, 2018, now Pat. No. 10,660,746, which is a
(Continued)

(51) Int. Cl.
*A61F 2/24* (2006.01)
*A61F 2/95* (2013.01)
*B65B 63/02* (2006.01)
*B65B 63/08* (2006.01)

(52) U.S. Cl.
CPC .......... *A61F 2/2409* (2013.01); *A61F 2/2418* (2013.01); *A61F 2/2427* (2013.01); *A61F 2/9525* (2020.05); *B65B 63/02* (2013.01); *B65B 63/08* (2013.01); *A61F 2/9522* (2020.05)

(58) Field of Classification Search
CPC ....... B65B 63/02; B65B 63/08; A61F 2/2418; A61F 2/2427; A61F 2/2409; A61F 2002/9522
See application file for complete search history.

(56) References Cited

U.S. PATENT DOCUMENTS

| | | | |
|---|---|---|---|
| 8,256,087 B2 | 9/2012 | Sokel et al. | |
| 8,479,380 B2 | 7/2013 | Malewicz et al. | |
| 8,562,663 B2 | 10/2013 | Mearns et al. | |

(Continued)

FOREIGN PATENT DOCUMENTS

| | | |
|---|---|---|
| WO | 2012/023979 | 2/2012 |
| WO | 2012/036742 | 3/2012 |

OTHER PUBLICATIONS

PCT/US2017/012447, The International Search Report and Written Opinion of the International Searching Authority, dated Apr. 24, 2017.

*Primary Examiner* — Moshe Wilensky
(74) *Attorney, Agent, or Firm* — Wentsler LLC

(57) ABSTRACT

Devices for, and methods of, compressing a stented prosthetic heart valve are disclosed. The method including inserting a stented prosthetic heart valve having a self-expandable stent frame into a container, initiating a cooling element in the container, transferring heat through a thermal conductor to cool an interior of the container, reducing a temperature of the self-expandable stent frame while located within the container to a critical temperature of not greater than 8° C., and compressing an outer diameter of the stented prosthetic heart valve while the stented prosthetic heart valve is at the critical temperature.

20 Claims, 7 Drawing Sheets

Related U.S. Application Data continuation of application No. 14/990,657, filed on Jan. 7, 2016, now Pat. No. 10,092,398.

(56)     References Cited

U.S. PATENT DOCUMENTS

| | | |
|---|---|---|
| 8,747,458 B2 | 6/2014 | Tuval et al. |
| 9,072,603 B2 | 7/2015 | Tuval et al. |
| 10,660,746 B2 | 5/2020 | Wang et al. |
| 2004/0199239 A1 | 10/2004 | Austin et al. |
| 2007/0162102 A1 | 7/2007 | Ryan et al. |
| 2008/0072653 A1 | 3/2008 | Gillick et al. |
| 2009/0292347 A1 | 11/2009 | Asmus et al. |
| 2011/0106246 A1 | 5/2011 | Malewicz et al. |
| 2011/0208296 A1 | 8/2011 | Duffy et al. |
| 2011/0214398 A1 | 9/2011 | Liburd et al. |
| 2011/0295216 A1 | 12/2011 | Miller |
| 2012/0083874 A1 | 4/2012 | Dale et al. |
| 2012/0245662 A1 | 9/2012 | Page |
| 2014/0000112 A1 | 1/2014 | Braido et al. |
| 2014/0215791 A1 | 8/2014 | Soundararajan et al. |
| 2014/0331475 A1 | 11/2014 | Duffy et al. |
| 2015/0040949 A1 | 2/2015 | Zucker et al. |
| 2015/0081011 A1 | 3/2015 | Young et al. |

PROSTHETIC HEART VALVE COOLING

CROSS-REFERENCE TO RELATED APPLICATIONS

This application is a Continuation of U.S. patent application Ser. No. 16/854,095, filed Apr. 21, 2020, which is a Continuation of U.S. patent application Ser. No. 16/123,047, filed Sep. 6, 2018, now U.S. Pat. No. 10,660,746, entitled "PROSTHETIC HEART VALVE COOLING", which is a Continuation of U.S. patent application Ser. No. 14/990,657, filed Jan. 7, 2016, now U.S. Pat. No. 10,092,398, entitled "PROSTHETIC HEART VALVE COOLING" the contents of each of which are incorporated herein by reference.

BACKGROUND

The present disclosure relates to implantable prosthetic heart valves. More particularly, it relates to prosthetic heart valves incorporating a stent and methods of compressing stented prosthetic heart valves for loading into a delivery system.

Various types and configurations of prosthetic heart valves are used to replace diseased natural human heart valves. The actual shape and configuration of any particularly prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprosthesis or mechanical heart valves prosthesis. As used throughout the specification, a "prosthetic heart valve" is intended to encompass bioprosthetic heart valves having leaflets made of a biological material (e.g., harvested porcine valve leaflets, or bovine, equine, ovine or porcine pericardial leaflets, small intestinal submucosa), along with synthetic leaflet materials or other materials.

Stented bioprosthetic heart valves have a frame (or stent) to which the biological valve material is attached. The biological valve members are sutured to the stent that provides support for the valve member in the patient's body. The stent prevents the biological valve members from collapsing and simplifies the insertion of the valve into the annulus of the patient after excision of the diseased valve. The stented bioprosthetic valve imitates the natural action of heart valves and provides a structure that is relatively compatible with the cardiovascular system. Stented prosthetic heart valves are believed to have important clinical advantages over mechanical or non-tissue prosthetic valves.

For many percutaneous delivery and implantation systems, the stent frame of the valved stent is made of a self-expanding material and construction. The stent frame is made of nitinol (a nickel and titanium alloy). With these systems, the valved stent is crimped down to a desired size and held in that compressed arrangement within an outer sheath, for example. Retracting the sheath from the valved stent allows the stent to self-expand to a larger diameter, such as when the valved stent is in a desired position within a patient.

Typically a stented transcatheter valve having a self-expanding frame, such as a nitinol based frame, is cooled prior to loading into the delivery system. The cooling process brings the valve out of the austenitic and into the martensitic phase. While in the martensitic phase, nitinol is more malleable. Often an ice bath based solution of approximately 4° C. is employed in order that the nitinol frame enters the martensitic state and becomes malleable and can be compressed for loading to a delivery system. In some stented transcatheter valves, the tissue used in the valve is in a "dry" state and is processed using glycerine, alcohols, other chemicals, and combinations thereof rather than a "wet" state and processed with excess glutaraldehyde. In valves including "dry" tissue, it is desirable to maintain the tissue in a dry state and avoid processes that use aqueous or liquid solutions. For dry tissue loaded onto a nitinol based frame or other self-expanding frame, it is desirable to cool the frame to a malleable, collapsible, state without exposing the tissue to an aqueous solution.

SUMMARY

One aspect of the present disclosure includes a method of compressing a stented prosthetic heart valve. The method including inserting a stented prosthetic heart valve having a self-expandable stent frame into a container. A cooling element is initiated in the container. Heat is transferred through a thermal conductor to cool an interior of the container. A temperature of the self-expandable stent frame is reduced while located within the container to a critical temperature. An outer diameter of the stented prosthetic heart valve is compressed while the stented prosthetic heart valve is at the critical temperature.

Another aspect of the present disclosure includes a method of loading a stented prosthetic heart valve to a transcatheter delivery system. The method includes inserting a stented prosthetic heart valve in an expanded state into a first chamber of a cooling vessel. Cooling is initiated in a second chamber of the cooling vessel. Heat is transferred from the first chamber to the second chamber through a thermally conductive wall to cool an interior of the first chamber. A temperature of the stented prosthetic heart valve is reduced to the critical temperature while located within the first chamber. The stented prosthetic heart valve is removed from the first chamber. The stented prosthetic heart valve is compressed while at the critical temperature. The compressed stented prosthetic heart valve is inserted into a delivery system.

DETAILED DESCRIPTION

The methods and devices of the present disclosure are useful in cooling a stented prosthetic heart valve having a self-expandable stent frame without exposing the stented prosthetic heart valve to liquid during cooling. The stented prosthetic heart valve or other device can be in a wet state or a dry state. The stented prosthetic heart valve or other device can desirably be processed and maintained in a dry state in accordance with aspects of the present disclosure. Regardless, in accordance with aspects of the present disclosure, the stented prosthetic heart valve is fluidly separated from the cooling element while positioned within the cooling device, and is thus, indirectly exposed to the cooling element. In other words, the stented prosthetic heart valve is not directly exposed to the cooling element during cooling. In accordance with the present disclosure, heat is removed from the stented prosthetic heart valve disposed in the cooling vessel via the cooling element disposed within the cooling vessel in isolation from the stented prosthetic heart valve.

Figure 1A:
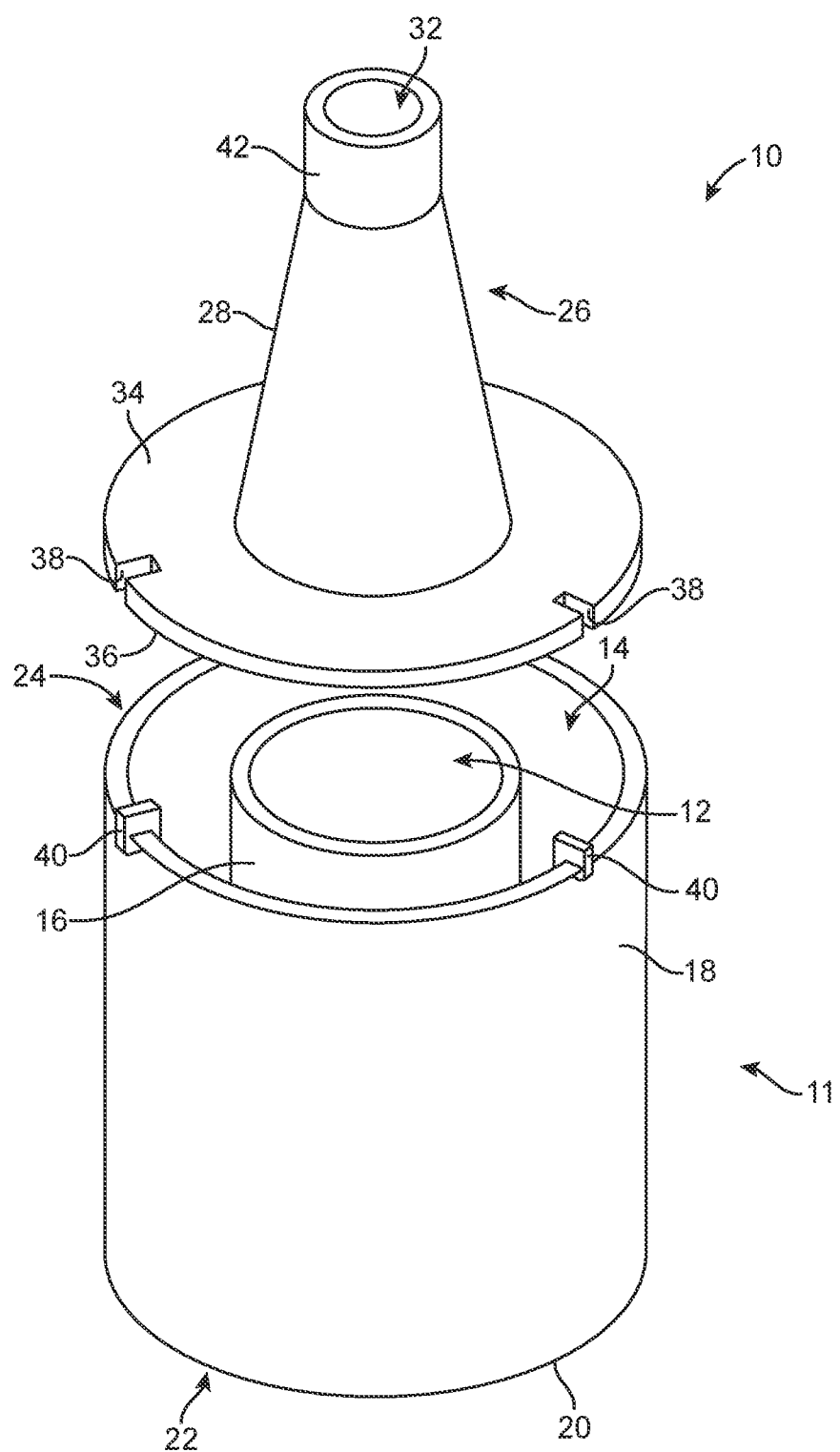
FIG. 1A is a perspective view of a cooling vessel in accordance with principles of the present disclosure.
Figure 1B:
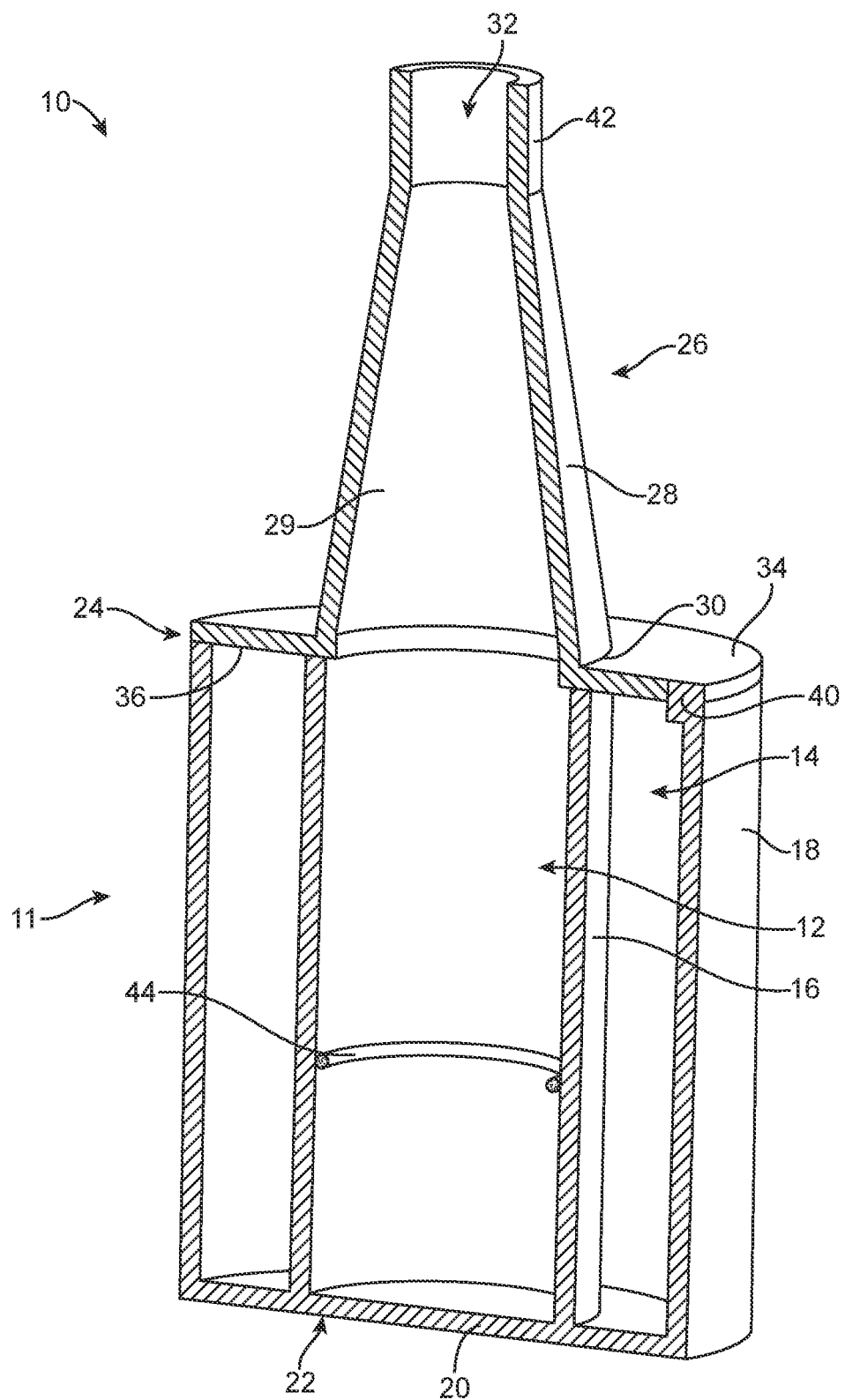
FIG. 1B is a perspective cross-sectional view of the cooling vessel of FIG. 1A in accordance with principles of the present disclosure.

FIGS. 1A and 1B illustrate perspective and cross-sectional views of a cooling device 10 useful in cooling a medical device such as a stented prosthetic heart valve in accordance with aspects of the present disclosure. The cooling device 10 is suitable to accommodate housing a cooling element and a stented prosthetic heart valve (not shown) separately. The cooling device 10 includes a cooling vessel 11 having a first chamber 12 suitable for containing the stented prosthetic heart valve separate from the second chamber 14 suitable for accommodating the cooling element. The first chamber 12 is sized and shaped to accommodate a single valve in both expanded and compressed states. A first, or inner, sidewall 16 defines a perimeter of the first chamber 12. The first sidewall 16 can be formed of a rigid, thermally conductive material such as stainless steel or ceramic, for example. The second chamber 14 is defined between the first sidewall 16 and a second, exterior, sidewall 18. In some embodiments, the cooling device 10 is cylindrical and the second chamber 14 has a larger diameter than the first chamber 12. In other words, in some examples, the second chamber 14 encircles the first chamber 12. The first sidewall 16 separates the first chamber 12 from the second chamber 14.

A bottom cap 20 extends across both the first and second chambers 12, 14 along lower wall edges of the first and second sidewalls 16, 18 to seal the chambers 12, 14 at a first end 22. The bottom cap 20 can be planar, stepped, or other surface shapes. The bottom cap 20 is suitable to provide a resting surface for placement of the cooling vessel 11 on a table or countertop, for example. The first and second chambers 12, 14 are fluidly separated from one another along the first sidewall 16 and the bottom cap 20. A second end 24, opposite the first end 22, provides access to the first and second chambers 12, 14.

In one embodiment, the first chamber 12 has a diameter that is at least slightly greater than the size of a single stented prosthetic heart valve (not shown) in a fully expanded state. The first chamber 12 is sized such that an air gap, or space, can be formed between the expanded heart valve and the first sidewall 16 when the heart valve is housed in the first chamber 16. The air gap can allow for a generally even conductance of cooling through the first sidewall 16, from the cooling element housed in the second chamber 14, to the valve in the first chamber 12. The second chamber 14 is sized to accommodate a cooling element and surround at least a side perimeter of the first chamber 12.

The cooling device 10 can include a top cap 26 operably removable from the cooling vessel 11. The top cap 26 can be coupled to the second end 24 of the cooling vessel 11. The top cap 26 is removable, or operable, to provide access to at least the first chamber 12. In some embodiments, the top cap 26 can provide access to both the first and second chambers 12, 14. The top cap 26 can include a funneling portion 28 extending above and away from the first chamber 12. In one embodiment, the funneling portion 28 is centrally positioned on the top cap 26. The funneling portion 28 is centrally aligned with the first chamber 12 when the top cap 26 is coupled to the cooling vessel 11. An interior 29 of the funneling portion 28 is fluidly open to the first chamber 12. The funneling portion 28 can be a truncated conical shape, for example, with a base 30 and a delivery port 32 opposite the base 30. The funneling portion 28 tapers inwardly from the base 30 to the delivery port 32. The base 30 has a diameter that is greater than a diameter of the delivery port 32. A diameter of the base 30 of the funneling portion 28 is approximately equal to the diameter of the first chamber 12. In one embodiment, the diameter of the base 30 of the funneling portion 28 is slightly smaller than the diameter of first sidewall 16. A rim 34 radially extends outward from the base of the funneling portion 28. A lower surface 36 of the rim 34 provides a coupling surface with the second end 24 of the cooling vessel 11. The funneling portion 28 can provide compression of the stented prosthetic heart valve during extraction of the cooled malleable valve from the first channel 12, passing through the funneling portion 28 and exiting through the delivery port 32 of the cooling device 10.

In some embodiments, the top cap 26 can be mated and aligned to the cooling vessel 11 when coupled. For example, the top cap 26 can include alignment slots 38 that can be matingly engaged with alignment tabs 40 of the cooling vessel 11. In some embodiments, the top cap 26 releasably, lockingly engages with the cooling vessel 11. A collar 42 can be included at the delivery port 32 of the funneling portion 28. The collar 42 is a circular segment of a diameter smaller than the base 30 diameter. In some embodiment, a lid or plug (not shown) may be included at the delivery port 32 to temporarily seal the interior of the funneling portion 28 and the first chamber 12 from ambient air and retain the cooled air in the first chamber 12 when the cooling element is initiated. A height of the top cap 26 can be substantially equivalent to a height of the cooling vessel 11, with both the top cap 26 and the cooling vessel 11 being at least slightly greater than a height of the stented prosthetic heart valve. The top cap 26 minimizes heat entering the first chamber 12 from the ambient air and cooling escaping from the first and second chambers 12, 14 into the ambient air during cooling.

With further reference to the cross-section of the cooling device 10 illustrated in FIG. 1B, an interior surface of the first sidewall 16 and bottom cap 20 within the first chamber 12 can include projections 44. The projections 44 are formed of a non-conductive material such as polymer, for example, or other non-conductive material. The projections 44 can assist in maintaining a valve a desired distance from the thermally conductive first sidewall 16. The projections 44 can assist in maintaining a valve centered within the first chamber 12. In FIG. 1B, a single ring-shaped projection 44 is illustrated as an example. The projections 44 can be ring-shaped, rounded bumps, or any other suitable shape.

The cooling device 10 is portable and can be handheld. The cooling device 10 is easily transportable into a surgical theater, for example, and is sterilizable. In one embodiment, the stented prosthetic heart valve is loaded into the cooling device 10, cooled, and compressed for loading onto a delivery system during the manufacturing process. In one embodiment, the stented prosthetic heart valve is inserted into the first chamber 12 of the cooling device 10 for cooling. One of the cooling systems described below is initiated causing the self-expandable frame of the stented prosthetic heart valve to cool to a critical malleable temperature. The critical temperature can vary based on the valve design and heat treatment process; however, a typical value can be 4-8° C. In one embodiment, the critical temperature is less than or equal to 10° C. (Celsius). The stented prosthetic heart valve remains fluidly separated from the cooling element during the entirety of cooling. The cooling devices in accordance with the present disclosure can be employed to remove heat from the first chamber 12 and the stented prosthetic heart valve removably contained within the first chamber 12. The first sidewall 16 is a thermal conductor. Heat is transferred from the first chamber 12 through the thermally conductive first sidewall 16 to cool the first chamber via the cooling element in the second chamber 14. The self-expandable stent frame of the stented prosthetic heart valve can be comprised of nitinol, for example. Nitinol is malleable at cool temperatures. The temperature of the self-expanding stent frame can be reduced to the critical temperature and the outer diameter of the stented prosthetic heart valve can be compressed while at the critical temperature. The stented prosthetic heart valve is extracted through the delivery port 32, and can be compressed during extraction through the funneling portion 28, for loading onto the delivery system. The stented prosthetic heart valve can then be packaged on the delivery system for use in the surgical theater. The stented prosthetic heart valve is fluidly separated from and indirectly exposed to the cooling element as described further below.

Figure 2A:
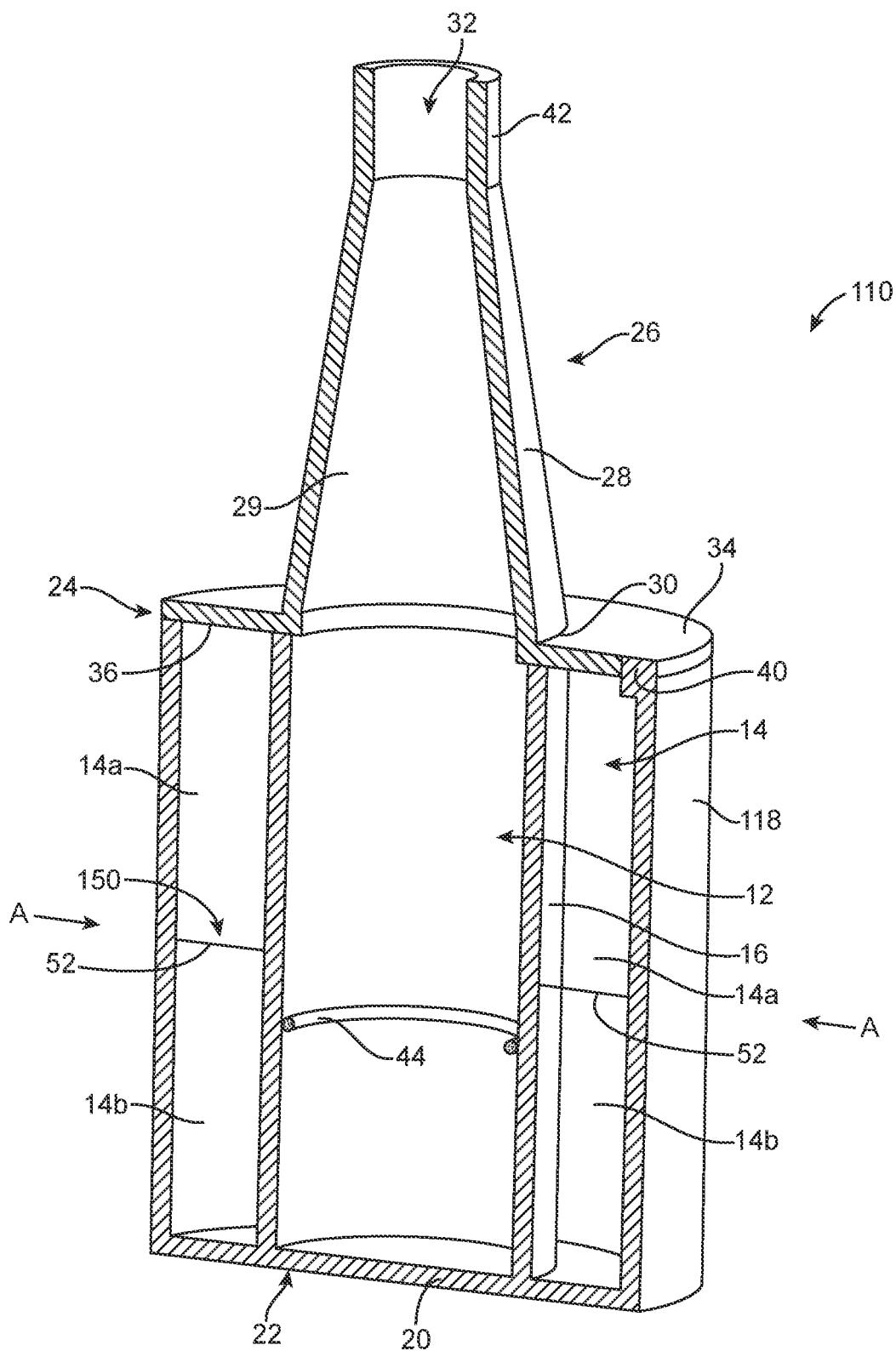
FIGS. 2A-2C are a schematic perspective views of exemplary cooling devices in accordance with principles of the present disclosure.

FIG. 2A is a cross-sectional illustration of a cooling device 110 including a cooling element 150 in accordance with principles of the present disclosure. Similar to the cooling device 10 of FIGS. 1A-1B and described above, the cooling device 110 includes the first chamber 12 suitable for removably containing the stented prosthetic heart valve and the second chamber 14 suitable for accommodating the cooling element 150. The first chamber 12 is sized and shaped to accommodate the valve in expanded and compressed states. The first sidewall 16 defines a perimeter of the first chamber 12 and is formed of a rigid, thermally conductive material. The second chamber 14 is defined between the first sidewall 16 and a second sidewall 118. In one embodiment, the cooling element 150 housed in the second chamber 14 is divided into two portions 14a, 14b with a thin barrier 52 fluidly separating the two portions 14a, 14b. The barrier 52 can be positioned and extend between the first sidewall 16 and the second sidewall 118. The barrier 52 can be positioned in any suitable manner to fluidly separate the two portions 14a, 14b within the second chamber 14. In one embodiment, the second sidewall 118 is flexible and can be manipulated with applied pressure. The barrier 52 can be pierced, broken, or otherwise ruptured by an application of pressure. For example, rupture or failure of the barrier 52 can be caused by squeezing of the second sidewall 118 and the barrier 52 inward as indicated by arrows "A" toward the first sidewall 16 until failure of the barrier 52 occurs. In one embodiment, water contained in the first portion 14a of the second chamber 14 is initially separated from chemicals (e.g., ammonium nitrate) contained in a second portion 14b. Upon failure of the barrier 52, an endothermic reaction occurs in response to a reaction of the chemicals from the second portion 14b contacting and mixing with water in the first portion 14a.

Figure 2B:
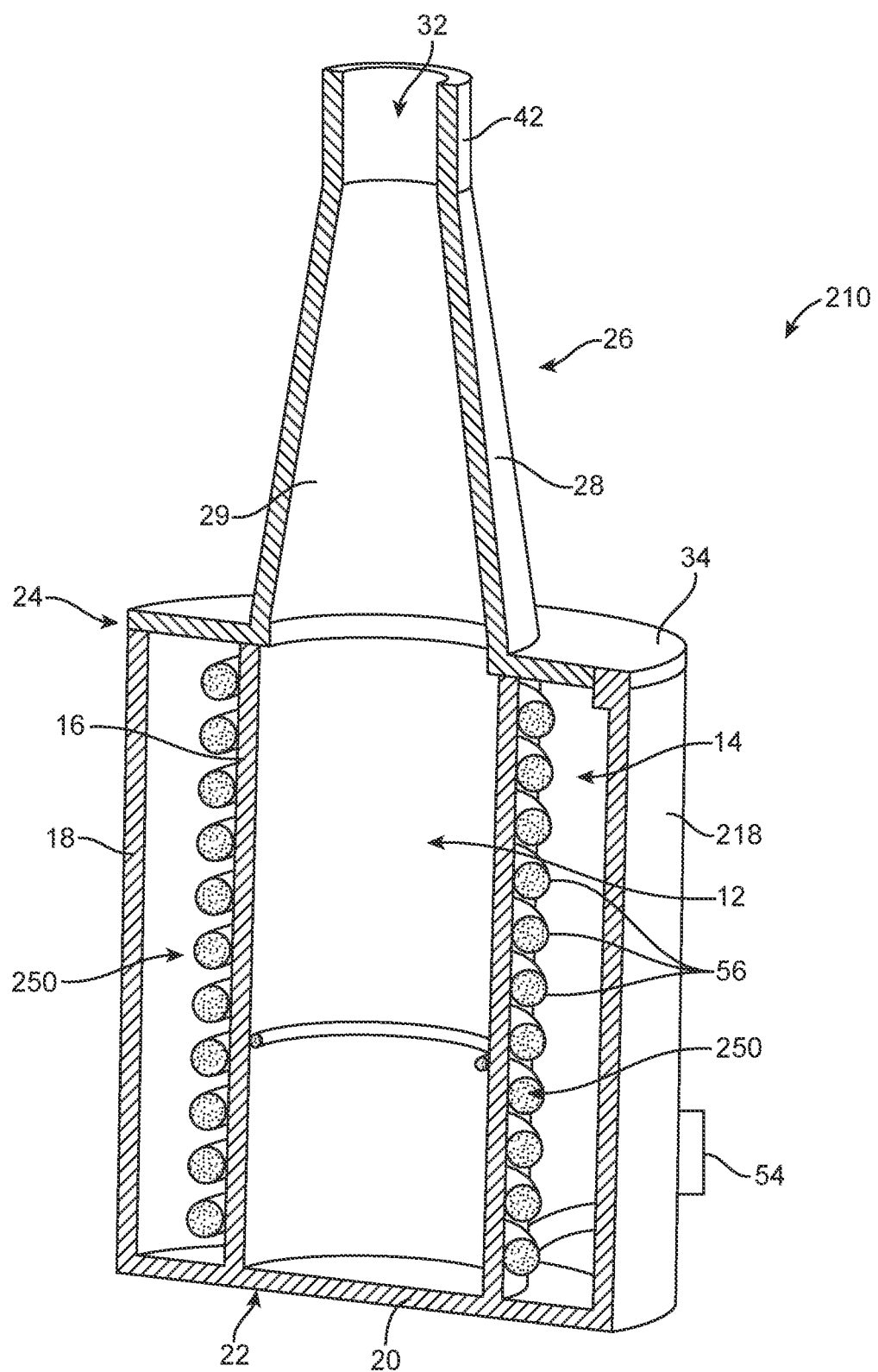

FIG. 2B is a cross-sectional illustration of a cooling device 210 including a cooling element 250 in accordance with principles of the present disclosure. The cooling device 210 includes a first chamber 12 suitable for removably containing the stented prosthetic heart valve and a second chamber 14 suitable for accommodating the cooling element 250. The first chamber 12 is sized and shaped to accommodate the valve in expanded and compressed states. The first sidewall 16 defines a perimeter of the first chamber 12 and is formed of a rigid, thermally conductive material. The second chamber 14 is defined between the first sidewall 16 and a second sidewall 218. In one embodiment, the second sidewall 218 is a rigid wall. An inlet port 54 is included providing at the second wall 218. The inlet port 54 can include a luer coupling or other appropriate coupling means suitable to connect for delivery of cooling fluid into an interior of the second chamber 14. The interior of the second chamber 14 can include coils 56 for circulating the coolant, or refrigerant such as Freon, for example, within the second chamber 14. In one embodiment, the coils 56 wrap around and contact the outer surface of the first sidewall 16. Heat is transferred from the first chamber 12 and the valve housed within the first chamber 12 upon initiating cooling of the cooling element 250.

Figure 2C:
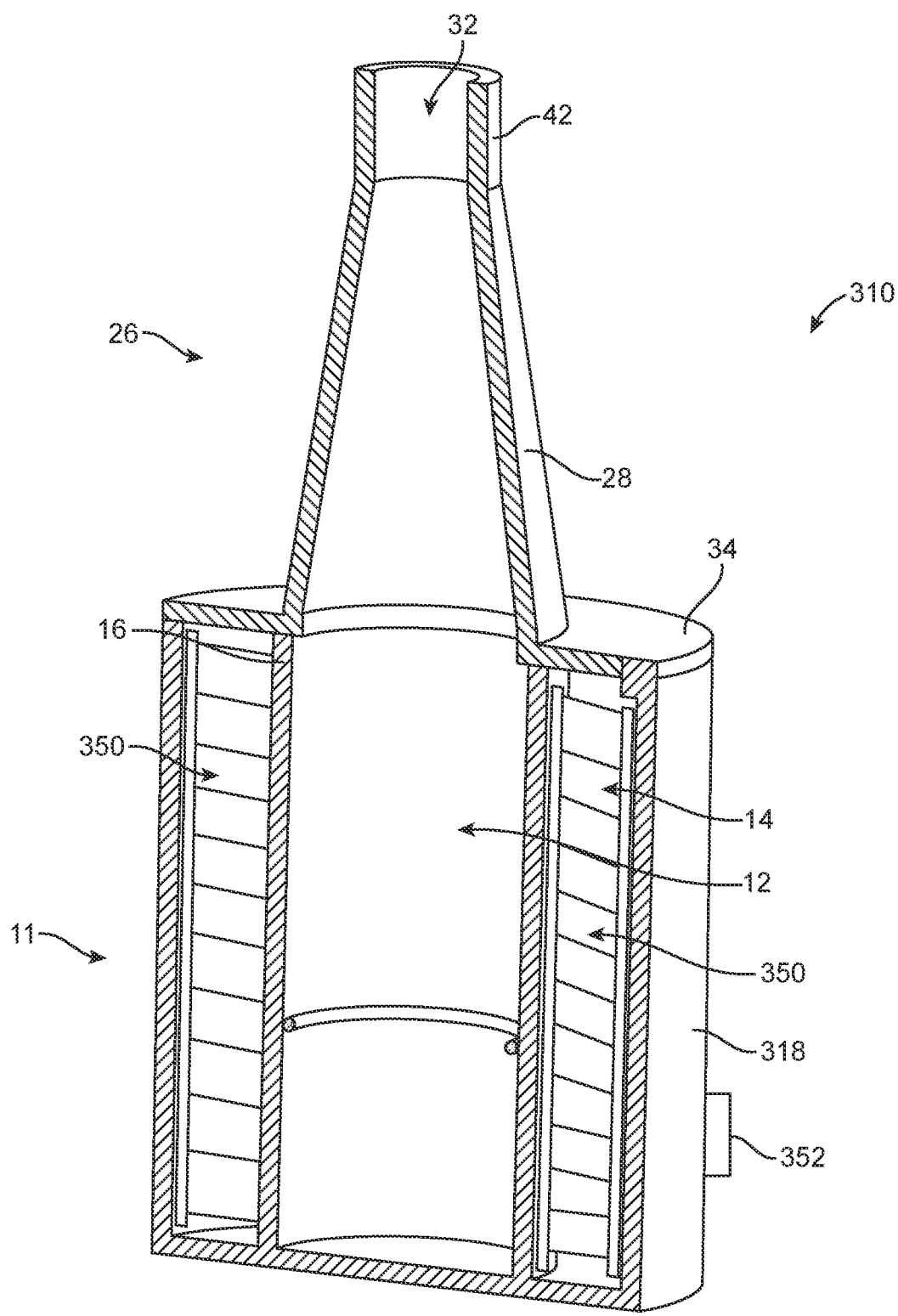

A cooling device 310 illustrated in FIG. 2C is similar to the cooling devices 110, 210 described above. The cooling device 310 includes a first chamber 12 suitable for removably containing the stented prosthetic heart valve and a second chamber 14 suitable for accommodating a cooling element 350. Cooling element 350 is a thermoelectric cooler (TEC). The first chamber 12 is sized and shaped to accommodate the valve in expanded and compressed states. A first sidewall 16 defines a perimeter of the first chamber 12. The first sidewall 16 can be formed of a rigid, thermally conductive material, for example, stainless steel or ceramic. The second chamber 14 is defined between the first sidewall 16 and a second sidewall 318. The second sidewall 318 is a rigid wall. A power source is coupled to the cooling device at a connection 352 positioned at the second wall 318 to power, or apply a voltage across, the TEC 350 to apply cooling to the first chamber 12 and valve housed therein. The TEC transfers heat from the first chamber 12, on the interior side of the TEC, to the exterior side of the TEC and second chamber 14 housing the TEC.

Figure 3A:
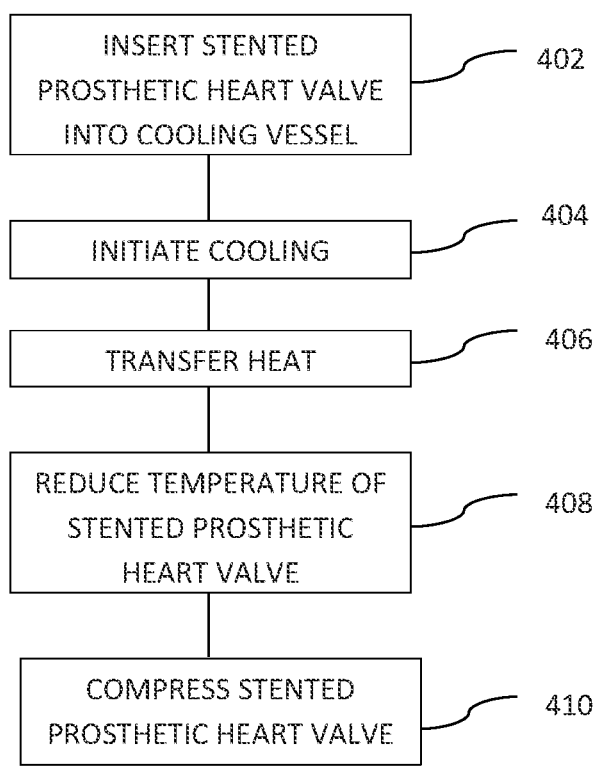
FIGS. 3A-3B are flow charts of methods of using a cooling device in accordance with principles of the present disclosure.

FIG. 3A is a flow chart of a method of compressing a stented prosthetic heart valve. The method includes a step 402 of inserting a stented prosthetic heart valve having a self-expandable stent frame into a cooling vessel. At step 404, a cooling element is initiated. At step 406, heat is transferred through a thermally conductive wall to cool an interior of the container. At step 408, the temperature of the self-expandable stent frame is reduced while located within the container to a critical temperature of not greater than 8° C. At step 410, an outer diameter of the stented prosthetic heart valve is compressed while the stented prosthetic heart valve is at the critical temperature.

Figure 3B:
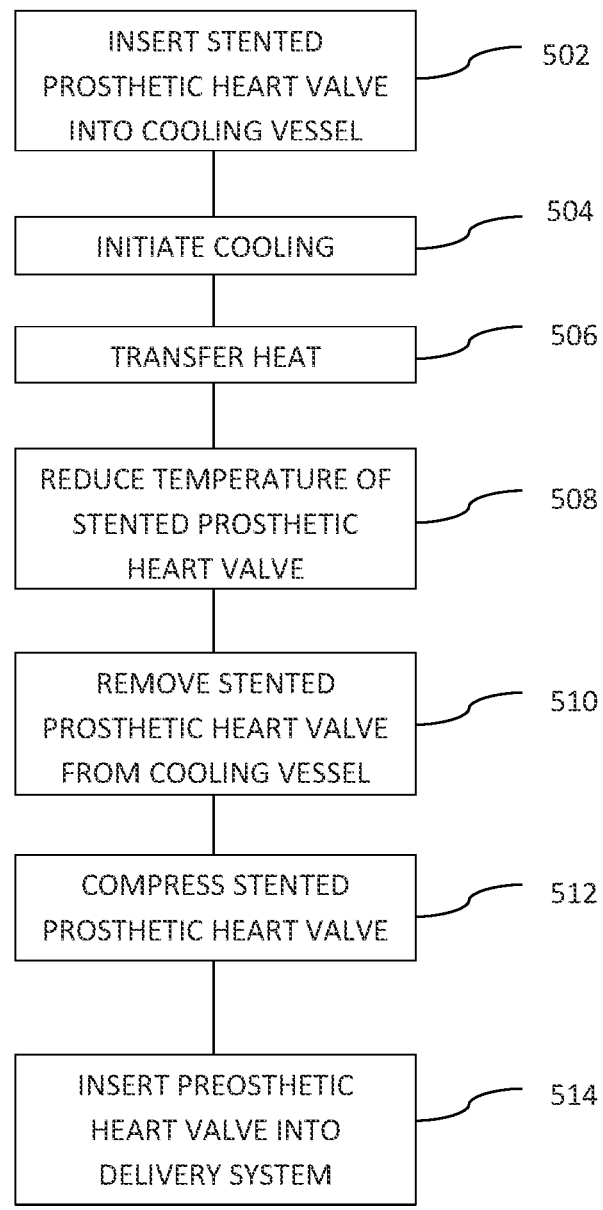

FIG. 3B is a flow chart of a method of loading a stented prosthetic heart valve to a transcatheter delivery system. The method includes a step 502 of inserting a stented prosthetic heart valve in an expanded state into a first chamber of a cooling vessel. The top cap 26 of the cooling device can be coupled to the cooling vessel after inserting the stented prosthetic heart vessel, isolating the valve from directly contacting a cooling element. At step 504, cooling is then initiated in a second chamber of the cooling vessel. In one embodiment, cooling is initiated by manually compressing the exterior of the cooling vessel to cause mixing of reagents for an endothermic reaction. In another embodiment, cooling is initiated with thermoelectric cooling. In another embodiment, cooling is initiated with circulating coolant in the second chamber of the cooling vessel. The circulating coolant, or other cooling element, is fluidly separated from the stented prosthetic heart valve within the cooling vessel during cooling. Regardless, of the manner of cooling, the valve is maintained in a dry state. At step 506, heat is transferred from the first chamber to the second chamber through a thermally conductive wall to cool an interior of the first chamber. At step 508, a temperature of the stented prosthetic heart valve is reduced while located within the first chamber to a critical temperature of not greater than 8° C. The step of reducing the temperature of the stented prosthetic heart valve includes the first chamber being free of liquid. At step 510, the stented prosthetic heart valve is removed from the first chamber. At step 512, the stented prosthetic heart valve is compressed while at the critical temperature. At step 514, the compressed stented prosthetic heart valve is inserted into, or mounted onto, a delivery system. Notably, steps 502-514 can be completed while maintaining the stented prosthetic heart valve in a dry state.

Although the present disclosure has been described with reference to preferred embodiments, workers skilled in the art will recognize that changes can be made in form and detail without departing from the spirit and scope of the present disclosure.

What is claimed is:

1. A device for compressing a stented prosthetic heart valve, the device comprising:
    an inner wall defining a dwell chamber sized and shaped for receiving an entirety of a stented prosthetic heart valve in an expanded state, the dwell chamber defining a leading side opposite a trailing side;
    an outer wall connected to and surrounding an exterior of the inner wall to define a cooling chamber between the inner and outer walls;
    a bottom wall extending across the trailing side of the inner wall, the bottom wall closing the dwell chamber at the trailing side;
    a cooling element maintained within the cooling chamber; and
    a cap extending from the leading side and defining a passageway open to the dwell chamber and closed to the cooling chamber, wherein a diameter of the passageway tapers in extension from the dwell chamber.

2. The device of claim 1, wherein the passageway terminates at a delivery port opposite the dwell chamber, and further wherein a diameter of the passageway at the delivery port is less than a diameter of the dwell chamber.

3. The device of claim 2, wherein the passageway is configured to compress a stented prosthetic heart valve as the prosthetic heart valve is extracted from the dwell chamber, along the passageway, and through the delivery port.

4. The device of claim 1, wherein the bottom wall extends across the outer wall to close the cooling chamber.

5. The device of claim 1, wherein the cap is removably assembled to the inner wall.

6. The device of claim 5, wherein the cap is removably assembled to the outer wall.

7. The device of claim 6, wherein the device is configured such that the cap closes the cooling chamber when assembled to the outer wall, and when the cap is disassembled from the outer wall, the cooling chamber is open.

8. The device of claim 1, wherein the cooling element includes first and second liquids that, when combined, generate an endothermic reaction.

9. The device of claim 1, wherein the cooling element includes a coil containing a refrigerant.

10. The device of claim 1, wherein the cooling element includes a thermoelectric cooler.

11. A combination stented prosthetic heart valve and compressing device, the combination comprising:
    a stented prosthetic heart valve; and
    a compressing device comprising:
        an inner wall defining a dwell chamber sized and shaped for receiving an entirety of the stented prosthetic heart valve in an expanded state, the dwell chamber defining a leading side opposite a trailing side,
        an outer wall connected to and surrounding an exterior of the inner wall to define a cooling chamber between the inner and outer walls,
        a bottom wall extending across the trailing side of the inner wall, the bottom wall closing the dwell chamber at the trailing side,
        a cooling element maintained within the cooling chamber,
        a cap extending from the leading side and defining a passageway open to the dwell chamber and closed to the cooling chamber, wherein a diameter of the passageway tapers in extension from the dwell chamber.

12. The combination of claim 11, wherein the combination is configured to provide a cooling state in which the stented prosthetic heart valve is maintained in the dwell chamber and the cooling element is operated to transfer heat from the dwell chamber to reduce a temperature of the stented prosthetic heart valve below a critical temperature.

13. The combination of claim 12, wherein the combination is further configured to provide a compressing state in which the stented prosthetic heart valve, maintained below the critical temperature, is extracted from the dwell chamber through the passageway to compress the stented prosthetic heart valve.

14. The combination of claim 11, wherein the bottom wall extends across the outer wall to close the cooling chamber.

15. A device for compressing a stented prosthetic heart valve, the device comprising:
    an inner wall defining a dwell chamber sized and shaped for receiving an entirety of a stented prosthetic heart valve in an expanded state, the dwell chamber defining a leading side opposite a trailing side;
    an outer wall connected to and surrounding an exterior of the inner wall to define a cooling chamber between the inner and outer walls;
    a cooling element maintained within the cooling chamber; and
    a cap extending from the leading side and defining a passageway open to the dwell chamber and closed to the cooling chamber, wherein a diameter of the passageway tapers in extension from the dwell chamber, and wherein the cap is removably assembled to the inner wall.

16. The device of claim 15, wherein the cap is removably assembled to the outer wall.

17. The device of claim 16, wherein the device is configured such that the cap closes the cooling chamber when assembled to the outer wall, and when the cap is disassembled from the outer wall, the cooling chamber is open.

18. The device of claim 15, wherein the passageway terminates at a delivery port opposite the dwell chamber, and further wherein a diameter of the passageway at the delivery port is less than a diameter of the dwell chamber.

19. The device of claim 18, wherein the passageway is configured to compress a stented prosthetic heart valve as the prosthetic heart valve is extracted from the dwell chamber, along the passageway, and through the delivery port.

20. A combination comprising the device of claim 15 and a stented prosthetic heart valve.

* * * * *